United States Patent [19]
Alpern et al.

[11] Patent Number: 5,230,424
[45] Date of Patent: Jul. 27, 1993

[54] MULTI-STRAND SUTURE PACKAGE AND COVER-LATCHING ELEMENT

[75] Inventors: Marvin Alpern, Glen Ridge; Jack Cascio, Bridgewater; David Demarest, Parsippany; Robert Duncan, Bridgewater; Konstantin Ivanov, Dunellen; Joseph Siernos, Whitehouse Station; Martin Sobel, Flemington, all of N.J.

[73] Assignee: Ethicon, Inc., Somerville, N.J.

[21] Appl. No.: 901,356

[22] Filed: Jun. 19, 1992

[51] Int. Cl.⁵ .............................................. A61B 17/06
[52] U.S. Cl. .................................. 206/63.3; 206/227; 206/380
[58] Field of Search ............... 206/63.3, 227, 380, 206/382

[56] References Cited

U.S. PATENT DOCUMENTS

| | | | |
|---|---|---|---|
| 4,424,898 | 1/1984 | Thyen et al. | 206/63.3 |
| 4,961,498 | 10/1990 | Kalinski et al. | 206/63.3 X |
| 4,967,907 | 11/1990 | Sobel et al. | 206/63.3 |
| 5,052,551 | 10/1991 | Cerwin et al. | 206/63.3 |
| 5,131,533 | 7/1992 | Alpern . | |

Primary Examiner—Bryon P. Gehman
Attorney, Agent, or Firm—Emil Richard Skula; James Riesenfeld

[57] ABSTRACT

A suture package is designed to facilitate automated loading of multiple needles and sutures into the package. The package includes a tray, for containing the needles and sutures, and a cover. The sutures are contained in a peripheral channel of the tray and an array of resilient cantilevered fingers prevent the sutures from lifting up out of the channel. Needle parks retain the needles that are attached to the sutures. In another embodiment of the invention, a package for retaining a wound suture and attached needle includes a tray for containing the needle and suture, including cover-latching elements that each have two vertical surfaces. Tabs on the removable cover each contact a surface of a corresponding latching element and have a free element that engages a shoulder of the element.

17 Claims, 4 Drawing Sheets

MULTI-STRAND SUTURE PACKAGE AND COVER-LATCHING ELEMENT

BACKGROUND OF THE INVENTION

1. Field of the Invention

This invention relates to a suture package designed to facilitate automated loading of multiple needles and sutures into the package.

2. Description of the Related Art

As in the case with many articles of manufacture, the requirements of the user of a surgical needle and suture——a surgeon or other health professional——limit the flexibility of the manufacturer. The goal is to design a package that meets the surgeon's requirements, while still being easy and inexpensive to manufacture.

In the packaging of surgical needles and sutures, it is important that the needle and its attached suture be easily removable from the package in one smooth motion. When the needle is grasped by a forceps and pulled, the needle should easily release from the package, and the suture should withdraw from the package smoothly, without binding or snagging in the package, and without becoming entangled. Also, suture materials, particularly monofilaments such as catgut, polydioxanone and the like, especially the heavier deniers, are known to take a set during storage; i.e., they tend to have a "memory" causing them to retain the shape of their position in the package after removal form the package. Hence the package should be designed to eliminate any tight bends or curves required in order to package the suture.

A package for holding a plurality of sutures and needles in spaced apart relationship and in the same plane was disclosed in U.S. Pat. No. 4,424,898, issued Jan. 10, 1984, to Thyen et al.

An "easy loading" suture package was described in coassigned copending U.S. appl. Ser. No. 843,651, filed Feb. 28, 1992, incorporated herein by reference. That package retains a needle and attached wound suture using cantilevered retaining fingers to prevent the suture from lifting up out of a retaining channel.

SUMMARY OF THE INVENTION

In accordance with the present invention, a tray for retaining a plurality of sutures and attached needles comprises:

a) a substantially planar base, having a peripheral outer wall,
b) a top joined to the base in a facing relationship, the top and base forming an inner wall and the inner and outer walls defining
   (i) a peripheral channel for containing the sutures and
   (ii) a central area surrounded by the channel,
c) an array of resilient cantilevered retaining fingers extending over the channel for preventing the sutures from lifting up out of the channel, an opening in the array permitting a first end of each suture to emerge from the channel, and
d) a plurality of needle parks in the central area for retaining needles attached to the first ends of the sutures.

A package for retaining needles and sutures comprises a tray as described above, and a removable cover over the top of the tray. In accordance with another embodiment of the present invention, a package for retaining a wound suture and attached needle comprises:

a) a tray for containing the suture and needle, including a plurality of cover-latching elements, each comprising two substantially parallel vertical surfaces separated by a gap, one of the surfaces having at or near its top a shoulder that extends into the gap, and
b) a removable cover on the tray, including a plurality of tabs, each of which extends from the cover, contacts a vertical surface of a corresponding latching element and has a free end that engages the underside of the shoulder.

The packages of the present invention are inexpensive to manufacture, particularly when made from molded thermoplastic, and are adapted for high-speed automated loading. They lend themselves to convenient and reliable dispensing of needles and sutures.

DETAILED DESCRIPTION OF THE INVENTION

Figure 1:
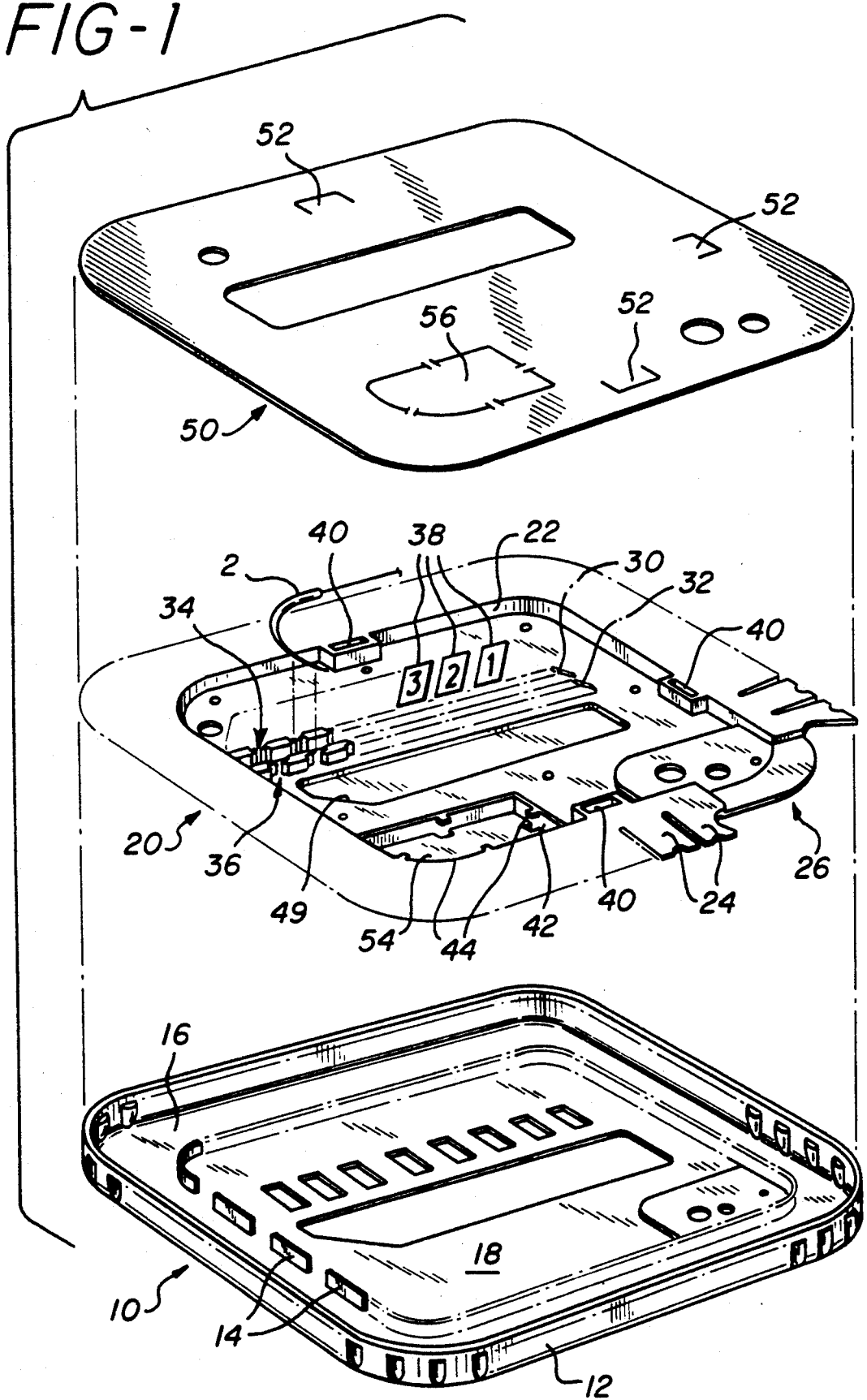
FIG. 1 is an exploded perspective view of a suture package of the present invention.

FIG. 1 depicts an exploded view of a suture package of the present invention. The package includes a base 10, top 20, and cover 50. Base 10 and top 20 are joined together to form a tray for a plurality of sutures and attached needles. Cover 50 is fit onto top 20 to contain and to identify the holder's contents. Base 10 is substantially planar, with a peripheral outer wall 12. Inner wall elements 14 of the base and 22 of the top form an inner wall which, together with outer wall 12, defines a peripheral channel 16 for containing sutures. Cantilevered retaining fingers 24 extend most of the way over channel 16 for preventing sutures from lifting up out of the channel. A gap 26 in the array of retaining fingers permits an end of the sutures to emerge from the channel.

The central area that lies within the inner wall includes a substantially planar area 18 of base 10 over which lies a substantially planar depressed area 28 of top 20. Parallel walls 30 and 32 on planar area 28 each have a series of spaced-apart gaps. The pairs of adjoining gaps form parks to retain needles, such as curved needle 2, shown above a pair of adjoining gaps 34 and 36. Optional needle-identifying numbers 38 adjoin each of the pairs of adjoining gaps in walls 30 and 32.

Optional latching elements 40 are gripped by corresponding die-cut tabs 52 after the tabs are pushed into the latching elements when cover 50 is pressed onto top 20 (see FIG. 2 and its description below). As cover 50 is pushed onto top 20, a die-cut identifying label may be transferred from cover 50 into an area surrounded by wall 42. Projections 44 on wall 42 capture label 54. The information on label 54 can be viewed through cutout 56 in cover 50.

Figure 2:
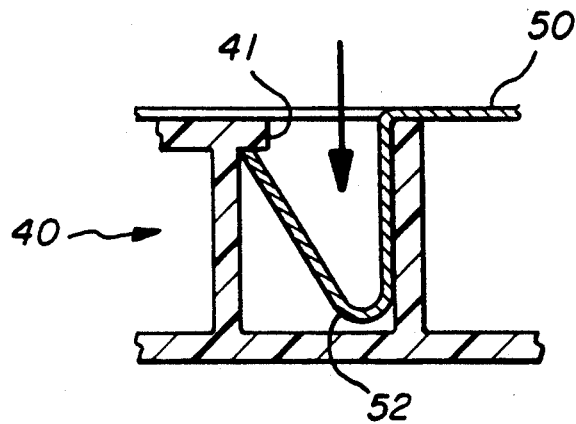
FIG. 2 is a cross-sectional view of a cover tab held in a cover-latching element.

FIG. 2 is a cross-sectional view showing the manner in which tab 52 is captured in latching element 40. During the package assembly process, tab 52 is forced into element 40 (as shown by the arrow) in such a way that tab 52 contacts a vertical surface of element 40 and its free end engages the underside of shoulder 41 of element 40. Preferably, tab 52 contacts at least the surface that is opposite to the surface that has shoulder 41 at its top. Although the means for attaching cover 50 to latching element 40 is shown in the context of this particular package, it is clear that the same attachment means would be suitable generally for removably attaching a cover to a tray for holding one or more needles and sutures. The cover-latching means depicted in FIG. 2 is simple and inexpensive to manufacture and provides firm and secure attachment of the cover to the tray.

Figure 3:
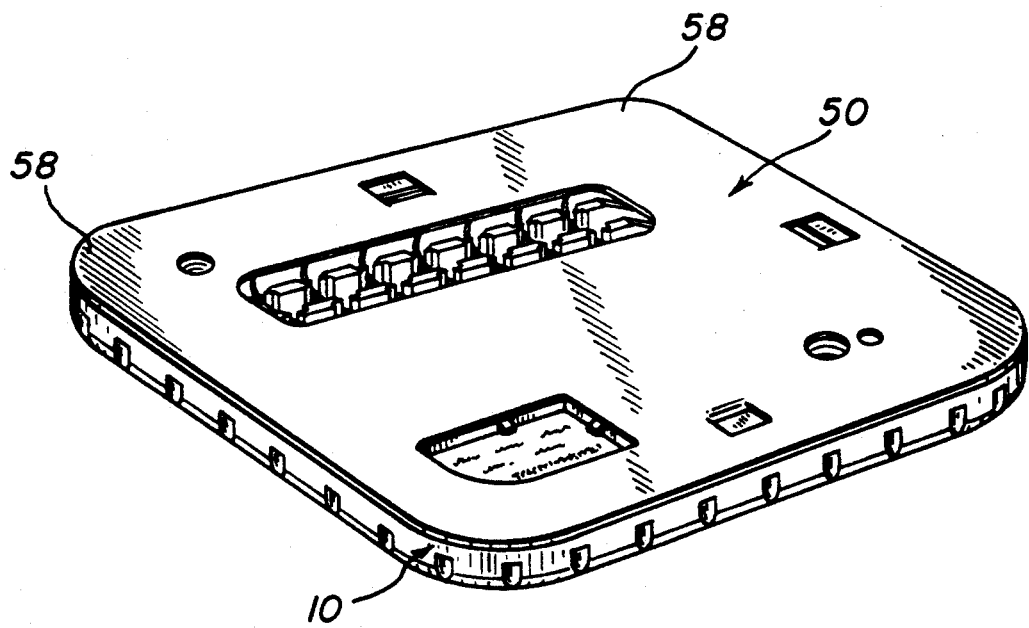
FIG. 3 is a perspective view of the suture package of FIG. 1 loaded with needles.

FIG. 3 is an isometric view of the assembled package of FIG. 1. An optional adhesive coating on all or part of the underside of base 10 (preferably covered by a release layer until ready for placement) permits the package to be releasably adhered to a surface, such as a mayo stand. To gain access to the contents of the package, a user lifts a corner 58 and removes cover 50. Alternatively cover 50 could have a scored diagonal tear line (not shown), in which case the user gains access to the package by grasping a corner and tearing the package open along the tear line. If the sutures are moisture sensitive (absorbable), they are generally hermetically sealed in a foil package (not shown), which is opened at a tear notch.

Figure 4:
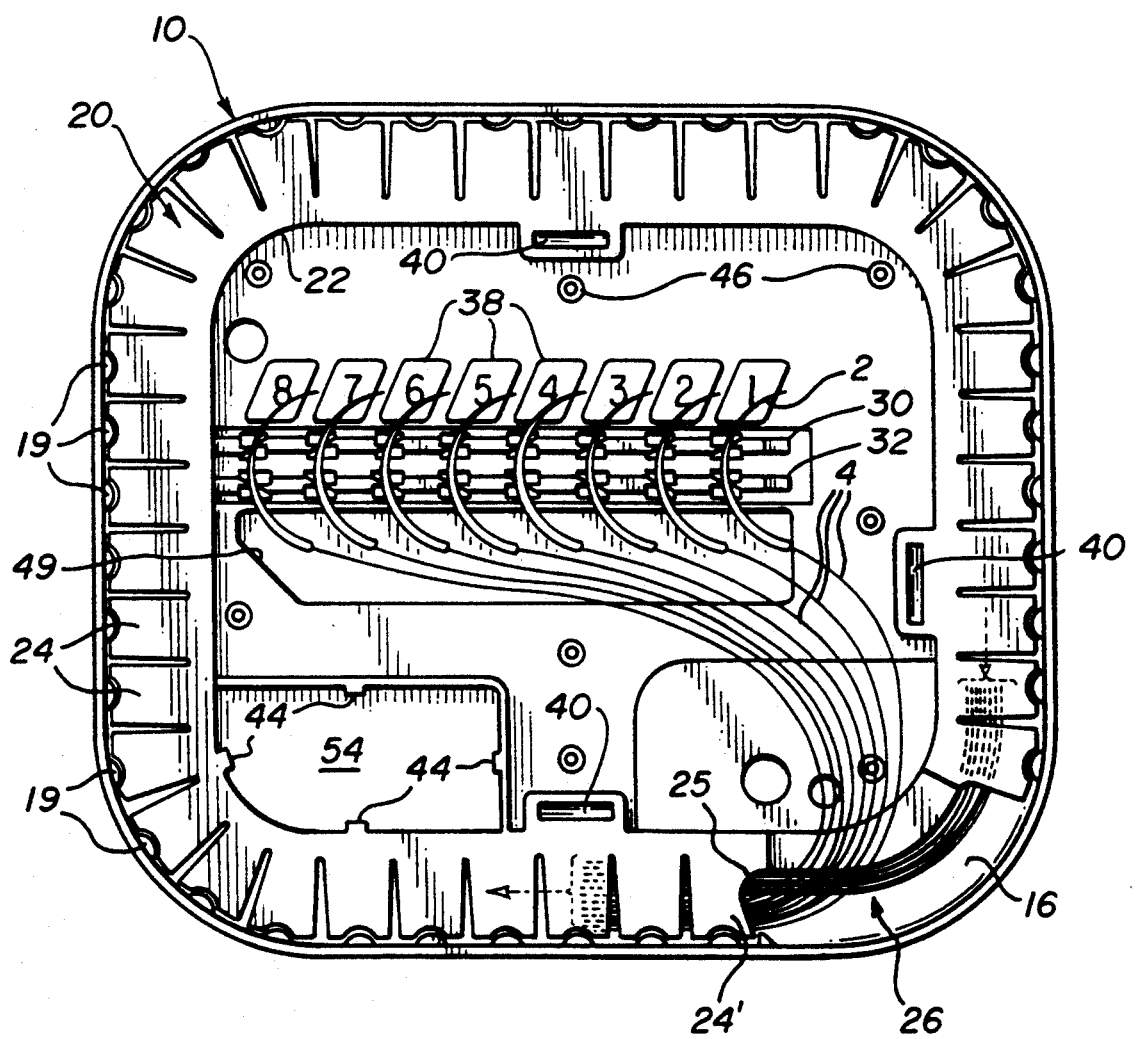
FIG. 4 is a top plan view of a needle and suture holder of the present invention.

FIG. 4 is a top view of a fully-loaded tray with the cover removed. The points at which top 20 has been attached to base 10 are denoted 46. The preferred attachment method is ultrasonic bonding, but other methods, such as heat bonding and adhesive bonding, are also suitable. To ensure that sutures 4 do not inadvertently lift out of channel 16, optional columns 19, corresponding to retaining fingers 24, extend inwardly from outer wall 12 toward the inner wall. To minimize potential damage to a suture as it is withdrawn, the retaining finger 24' that borders the gap 26 in the array of fingers has a rounded edge 25.

Figure 5:
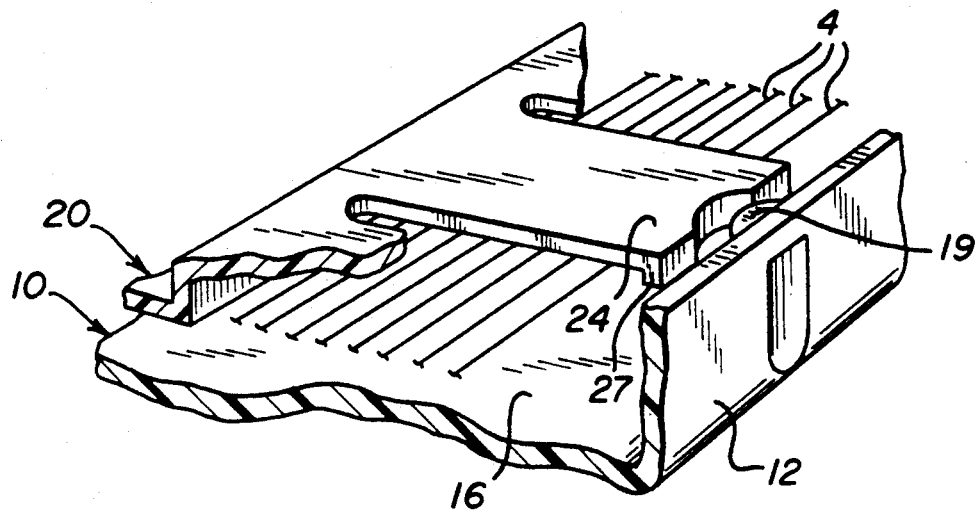
FIG. 5 is an enlarged cutaway view of suture-retaining elements.

FIG. 5 is an enlarged cutaway section view of the suture retaining elements. Note that both the fingers and optional columns may have a variety of configurations, but the columns are shaped to leave between finger and column a narrow gap whose geometry minimizes the chances of suture escape. Additional protection against suture escape, particularly the escape of the suture "tail," is provided by optional downward-extending lip 27.

Figure 6:
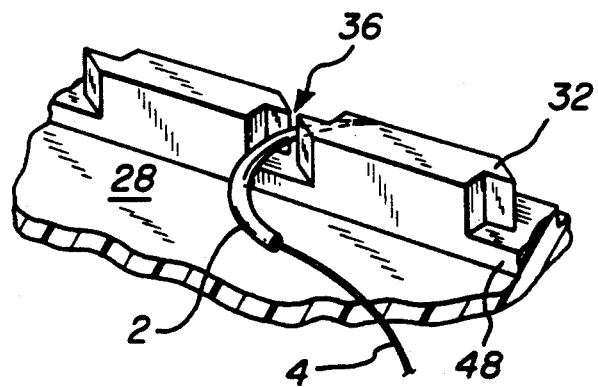
FIG. 6 is an enlarged cutaway view of a needle in a needle park.

FIG. 6 shows an enlarged cutaway view of part of a needle park, with a needle 2 in gap 36 of wall 32. To remove needle 2 and attached suture 4 from the park, the needle is first grasped with a needle holder. Grasping a needle with a needle holder is facilitated by the presence of low wall 48, which keeps the needles raised above the depressed floor area 28. Grasping a needle closer to its point of attachment to the suture is facilitated by the optional trapezoidal-shaped area 49 (shown in FIGS. 1 and 4), which is depressed below the level of planar area 28. Once firmly grasped in the needle holder, the needle is removed from the needle park and the attached suture is withdrawn from channel 16.

A variety of materials can be used for the tray and cover of the present suture package. Preferably, the tray is formed of a molded thermoplastic material. Molding is a preferred forming method because it provides adequate tolerance and detail at low cost per unit. Suitable tray materials include polyester, polyvinyl chloride, polyethylene, polystyrene, and polypropylene. Polypropylene is preferred, particularly when the top is to be ultrasonically attached to the base. The cover is preferably made of paper. As was discussed above, the package is hermetically sealed in foil if the sutures are absorbable. A simple overwrap suffices for non-absorbable sutures.

I claim:

1. A tray for retaining a plurality of sutures and attached needles comprising:
   a) a substantially planar base, having a peripheral outer wall,
   b) a top joined to the base in a facing relationship, the top and base forming an inner wall and the inner and outer walls defining
      i) a peripheral channel for containing sutures and
      ii) a central area surrounded by the channel,
   c) an array of resilient cantilevered retaining fingers extending over the channel for preventing contained sutures from lifting up out of the channel, an opening in the array permitting a first end of each suture to emerge from the channel, and
   d) a plurality of needle parks in the central area for retaining needles attached to the first ends of contained sutures.

2. The tray of claim 1 in which the central area comprises a substantially planar area of the base coplanar with a floor of the channel and a depressed substantially planar area of the top that overlies the planar area of the base.

3. The tray of claim 1 in which the retaining fingers extend from the inner wall most of the way across the channel toward the outer wall.

4. The tray of claim 3 in which the retaining fingers each have a downward-extending lip at or near the end of the finger near the outer wall.

5. The tray of claim 3, further comprising a plurality of columns, each corresponding to a retaining finger and extending from the outer wall toward the inner wall.

6. The tray of claim 1 in which an end of the opening in the array of retaining fingers is formed by a rounded edge of a retaining finger.

7. The tray of claim 1 in which the needle parks comprise first and second substantially parallel walls on the central area, the walls each having a plurality of spaced apart gaps such that gaps in the first wall adjoin gaps in the second wall and permit each needle to be retained in a pair of adjoining gaps.

8. The tray of claim 7 in which the central area is marked with an identifying number adjoining each pair of gaps.

9. The tray of claim 1 in which the tray comprises a molded thermoplastic material.

10. The tray of claim 9 in which the thermoplastic material is selected form the group consisting of polyester, polyvinyl chloride, polyethylene, polystyrene, and polypropylene.

11. The tray of claim 10 in which the thermoplastic material is polypropylene.

12. The tray of claim 1 further comprising an adhesive coating on the underside of the base to permit the package to be releasably adhered to a surface.

13. A package for retaining needles and sutures comprising the tray of claim 1 and a removable cover over the top of the tray.

14. The package of claim 13 in which the tray further comprises a plurality of latching elements and the cover further comprises a plurality of die-cut tabs that grip corresponding latching elements when the cover is on the tray.

15. The package of claim 13 in which the tray further comprises a plurality of horizontal projections elevated above the central area to capture an identifying label, and the cover has a cutout through which the label may be read.

16. A package for retaining a wound suture and attached needle comprising:

a) a tray for containing a suture and needle, including a plurality of cover-latching elements, each comprising two substantially parallel vertical surfaces separated by a gap, one of the surfaces having at or near its top a shoulder that extends into the gap, and b) a removable cover on the tray, including a plurality of tabs, each of which extends from the cover, contacts both vertical surfaces of a corresponding cover-latching element, and has a free end that engages the underside of the corresponding shoulder.

17. The package of claim 16 in which the tray comprises a molded thermoplastic material.

* * * * *